United States Patent [19]

Suzukamo et al.

[11] Patent Number: 4,644,080

[45] Date of Patent: Feb. 17, 1987

[54] METHOD FOR RACEMIZATION OF CHRYSANTHEMIC ACID OR ITS ESTER

[75] Inventors: Gohfu Suzukamo, Ibaraki; Masami Fukao, Shiga, both of Japan

[73] Assignee: Sumitomo Chemical Co., Ltd., Osaka, Japan

[21] Appl. No.: 702,599

[22] Filed: Feb. 19, 1985

[30] Foreign Application Priority Data

Feb. 22, 1984 [JP] Japan ................................ 59-31861
Jun. 18, 1984 [JP] Japan ............................... 59-125893

[51] Int. Cl.$^4$ ................. C07C 67/333; C07C 51/353
[52] U.S. Cl. .................................... 560/124; 562/401; 562/506
[58] Field of Search ................. 560/124; 562/506, 401

[56] References Cited

U.S. PATENT DOCUMENTS

| | | |
|---|---|---|
| 3,794,680 | 2/1974 | Matsui ................................ 562/506 |
| 3,989,750 | 11/1976 | Nagase ............................... 562/506 |
| 4,182,906 | 1/1980 | Suzukamo ........................... 562/506 |
| 4,473,703 | 9/1984 | Suzukamo ........................... 562/506 |
| 4,485,257 | 11/1984 | Suzukamo ........................... 562/506 |

FOREIGN PATENT DOCUMENTS 62979 10/1982 European Pat. Off. ............ 562/506

Primary Examiner—Michael L. Shippen
Attorney, Agent, or Firm—Birch, Stewart, Kolasch and Birch

[57] ABSTRACT

The present invention relates to a method for racemization of a chrysanthemic acid or its ester, which comprises contacting the acid or its ester with a boron bromide compound, optionally in the presence of organic hydroperoxide.

19 Claims, No Drawings

METHOD FOR RACEMIZATION OF CHRYSANTHEMIC ACID OR ITS ESTER

The present invention relates to a method for racemization of a chrysanthemic acid or its ester. More particularly, it relates to a method for racemization of an optically active chrysanthemic acid or its ester of the formula:

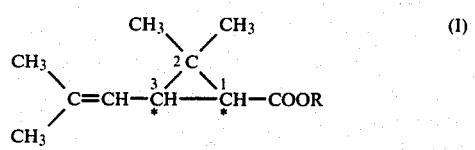

wherein R is a hydrogen atom; an alkyl group which may be substituted with a cycloalkyl group or with an aryl group, said alkyl group having from 1 to 20 total carbon atoms including the substituent; or a cycloalkyl group which may be substituted with an alkyl or with an alkoxy group, said cycloalkyl group having from 5 to 20 total carbon atoms including the substituent, which comprises contacting the acid or its ester with a boron bromide compound.

The chrysanthemic acid, i.e. 2,2-dimethyl-3-(2-methyl-1-propenyl)cyclopropane-1-carboxylic acid, constitutes the acid component of the esters well-known as the so-called pyrethroidal insecticides, such as pyrethrin, allethrin, phthalthrin, etc., which are utilized as low mammalian toxic, quickly effective insecticides, and is useful as intermediate of these esters.

The chrysanthemic acid has four kinds of isomers, that is, two geometrical isomers, i.e. cis and trans forms, which respectively have two kinds of optical isomers, i.e. (+) and (−) forms. It has been known that, in general, among the isomers the esters composed of a trans-form acid exhibit stronger insecticidal activity than those composed of a corresponding cis-form acid. Furthermore, the esters composed of a (+)-form acid exhibit exceedingly higher activity than those composed of the corresponding (−)-isomer.

In general, the chrysanthemic acid is industrially produced as a mixture of cis and trans forms, each of which is in the form of racemic mixture, namely, as (±)-form. The optical resolution of the thus-synthesized acid by means of an optically active organic base is conducted to obtain the (+)-form acid which is utilized for the preparation of insecticidal compounds with a high activity. The remaining (−)-isomer after the optical resolution is least useful, since the esters composed thereof are almost inactive. Accordingly, it is a problem to be solved in the production of the (+)-form acid, particularly in a commercial scale, that the (−)-form acid be racemized with a high efficiency, so as to be utilized again as a material for the optical resolution mentioned above.

The racemization of the optically active chrysanthemic acid is difficult, since it possesses two asymmetric carbon atoms, as shown above, at the 1- and 3-positions (exhibited by * marks).

Some methods for the racemization have so far been studied. Thus, in one method the (−)-trans-chrysanthemic acid is oxydized at its $C_3$-substituted isobutenyl group to convert into a keto-alcohol group, and the acid group at the $C_1$-position is converted into a lower alkyl ester, which is then subjected to a reaction with an alkali metal alcoholate in a solvent (U.S. Pat. No. 3,282,984). In a second method a (−)-trans-chrysanthemic acid is irradiated with ultraviolet rays in the presence of a photosensitizer (U.S. Pat. No. 3,657,086). In a third method an optically active chrysanthemic acid is converted into the corresponding acid halide and then contacted with a Lewis acid (U.S. Pat. Nos. 3,989,750 and 4,182,906). In a fourth method an optically active chrysanthemic acid is converted into a acid anhydride and then contacted with an iodine (U.S. Pat. No. 4,485,257).

As a result of an extensive study, the inventors have now found that optically active chrysanthemic acid or its ester of formula (I) can be conveniently racemized by the treatment with a boron bromide compound and that the said racemization can be accomplished more readily and in high yield by adding an organic hydroperoxide. This invention is based on such finding.

According to the present invention, the optically active chrysanthemic acid or its ester can be racemized readily and in high yield and the method of the present invention is very convenient for the racemization, particularly in commercial scale. Moreover, the present invention enables the direct utilization of (−)-chrysanthemic acid or its ester, which is separated off in the procedures of optical resolution, with high efficiency.

In the method of the present invention, the use of an organic hydroperoxide brings a remarkable reduction in the amount of a boron bromide compound used for the racemization as well as an extraordinary reduction of the reaction time. The use of an organic hydroperoxide, in particular, can remarkably produce good results in the case of the use of chrysanthemic acid as the starting material.

This racemization method always gives the trans-rich reaction product regardless of the isomeric composition of the starting material. Since the insecticidal activity of the pyrethroidal esters in the trans form is generally higher than that of the corresponding esters in the cis form, the above characteristic feature of the racemization method is of great advantage. Thus, the racemization method may be also applied to the conversion of the racemic cis isomer or of a mixture of the racemic cis and trans isomers of the acid or its ester to the corresponding racemic trans-rich isomer.

The method of the present invention will more fully be described hereinafter.

In the present invention, any of the four optical isomers of chrysanthemic acid or its ester can be used solely or in mixtures of an optional proportion as the starting material. The starting material of any degree of optical purity can be employed. Needless to say, however, employment of the starting material of (−)-form or rich in (−)-form makes the object of the present invention significant.

As the boron bromide compound used in the method of the present invention, there may be typically illustrated boron tribromide.

The boron bromide compound may be used in amount of 1/2000 to ¼ mol, preferably 1/1000 to 1/10 mol, based upon a mol of the starting material to be treated.

As the organic peroxide, there may be illustrated as below.

(1)

Aliphatic hydroperoxide Hydroperoxide produced by oxidation of ethers such as tetrahydrofuran, dioxane or the like, tert-Butyl hydroperoxide, 1,1,3,3-Tetramethyl butyl hydroperoxide, p-Methane hydroperoxide, etc.

(2)

Aromatic hydroperoxide Cumene hydroperoxide Diisopropylbenzene hydroperoxide, etc.

The amount of the organic hydroperoxide to be used, in general, can range from 1/10 to 5 mol, preferably ¼ to 2 mol, based upon a mol of the boron bromide compound used.

In carrying out the present racemization reaction, an inert solvent may preferably be used. For such solvents, there may be illustrated saturated aliphatic hydrocarbons, aromatic hydrocarbons and their halide compounds, ethers, etc.

The presence of water, acid, alcohol or the like in the reaction medium does not undesirably influence the present reaction, as long as the amount thereof is small.

The reaction temperature may generally be chosen arbitrarily within the range from $-30°$ C. to $100°$ C.

The reaction time is more or less associated with the amount of materials to be used and the reaction temperature. Usually the object would be well achieved within a period of time ranging from a few minutes to 10 hours.

In carrying out the present racemization reaction in the presence of organic hydroperoxide, the following procedure is generally employed. One is the procedure in which a boron bromide compound is added into a mixture of the starting material to be treated and an organic hydroperoxide in a solvent, and the other is the procedure in which an organic hydroperoxide and a boron bromide compound are in parallel added into the starting material to be treated in a solvent.

The process of the reaction can be checked by the measurement of the optical rotation, gas-chromatography, etc.

As described above, by the method of the present invention the racemization of the $(-)$-isomer of the optically active chrysanthemic acid or its ester can be readily and economically accomplished in commercial scale. The thus racemized product may be subjected to optical resolution procedures to obtain the useful $(+)$-isomer of chrysanthemic acid or its ester.

Moreover, the racemization method of the present invention can be also applied to the conversion of the racemic cis isomer or of a mixture of the racemic cis and trans isomers of the chrysanthemic acid or its ester to the more useful corresponding racemic trans-rich isomer.

The method of the present invention will be further illustratively shown in the following examples.

EXAMPLE 1

In a 50 ml flask, there were charged $(-)$-cis-chrysanthemic acid (2.0 g), and n-hexane (18.0 g) under nitrogen. Boron tribromide (0.3 g) was added thereto at $15°$ C. and stirred for 1 hour.

Ice water was added to the reaction mixture and stirred to decompose the catalyst. The separated organic layer was extracted twice with a 10% sodium hydroxide aqueous solution (4.8 g). The aqueous layer was acidified with diluted hydrochloric acid and extracted twice with toluene. The toluene layer was washed with water and dried over sodium sulfate. The solvent was evaporated and the residue was distilled (b.p. $110°$–$119°$ C./2.5 mmHg) to obtain 1.38 g of distillate. The IR spectrum of the product was identical with that of chrysanthemic acid. The composition of the optical isomers in the product was determined by gas chromatography after conversion into $(+)$-2-octyl ester. The result was as follows : $(+)$-cis, 3.3%; $(-)$-cis, 4.4%; $(+)$-trans, 45.7%; $(-)$-trans, 46.6%.

EXAMPLE 2

In a 50 ml flask, there were charged $(-)$-cis-ethyl chrysanthemate (2.0 g) and n-heptane (18.0 g) under nitrogen. Boron tribromide (0.26 g) was added thereto at $15°$ C. with stirring and stirred for 3 hours. The reaction mixture was washed with ice water. The solvent was evaporated under reduced pressure to leave a residue (1.96 g). The residue was added to a 10% sodium hydroxide aqueous solution (10.2 g) and refluxed for 3 hours. The aqueous layer was washed with toluene. The aqueous layer was acidified with diluted hydrochloric acid and extracted with toluene. The toluene layer was washed with water and dried over anhydrous sodium sulfate. The solvent was evaporated under reduced pressure to leave a residue (1.6 g). The residue was distilled (b.p. $110°$–$119°$ C./2.5 mmHg) to obtain 1.53 g of distillate. The IR spectrum of the product was identical with that of chrysanthemic acid. The composition of the optical isomers in the product was determined by the same method as described in EXAMPLE 1. The result was as follows: $(+)$-cis, 3.3%; $(-)$-cis, 4.3%; $(+)$-trans, 46.1%; $(-)$-trans, 46.3%.

EXAMPLE 3

In a 50 ml flask, there were charged ethyl chrysanthemate (composition: $(+)$-cis, 2.5%; $(-)$-cis, 16.8%; $(+)$-trans, 12.3%; $(-)$-trans, 68.4%) (2.0 g) and n-heptane (18.0 g) under nitrogen. Boron tribromide (0.26 g) was added thereto at $15°$ C. with stirring and stirred for 3 hours. The reaction mixture was washed with ice water. The solvent was evaporated under reduced pressure to leave a residue (1.95 g). The residue was distilled ($85°$–$88°$ C./10 mmHg) to obtain a distillate (1.77 g). The IR spectrum of the product was identical with that of ethyl chrysanthemate. A small amount of the product was hydrolyzed by usual method to obtain chrysanthemic acid. The composition of the optical isomers in the product was determined by the same method as described in EXAMPLE 1. The result was as follows: $(+)$-cis, 2.7%; $(-)$-cis, 3.0%; $(+)$-trans, 46.6%; $(-)$-trans, 47.7%.

EXAMPLE 4

In a 50 ml flask, there were charged ethyl chrysanthemate (composition: $(+)$-cis, 2.5%; $(-)$-cis, 16.8%; $(+)$-trans, 12.3%; $(-)$-trans, 68.4%) (2.0 g) and dioxane (18.0 g) under nitrogen. Boron tribromide (0.26 g) was added thereto at $15°$ C. with stirring and stirred for 4 hours. Then a small amount of the reaction mixture was hydrolyzed to obtain chrysanthemic acid. The composition of the optical isomers in the product was determined by the same method as described in EXAMPLE 1. The result was as follows: $(+)$-cis, 2.4%; $(-)$-cis, 2.6%; $(+)$-trans, 46.2%; $(-)$-trans, 48.8%.

EXAMPLE 5

In a 50 ml flask, there were charged chrysanthemic acid (composition: $(+)$-cis, 3.0%; $(-)$-cis, 22.0%; $(+)$-trans, 11.8%; $(-)$-trans, 63.2%) (5.0 g), toluene (9.0 g) and t-butyl hydroperoxide (0.027 g) under nitrogen. A solution of boron tribromide (0.15 g) in toluene (2.6 g) was added thereto at $15°$–$20°$ C. with stirring. After 30 minutes, the composition of the optical isomers of chrysanthemic acid in the reaction solution was checked by gas chromatography after conversion into (+)-2-octyl ester (composition: (+)-cis, 2.1%; (−)-cis, 2.1%; (+)-trans, 47.3%; (−)-trans, 48.5%). After 1 hour, the reaction mixture was washed with diluted hydrochloric acid. 10% Sodium hydroxide aqueous solution (17.9 g) was added to the mixture at 40° C. with stirring and the aqueous layer was separated. The aqueous layer was acidified with diluted sulfuric acid and extracted with toluene. The toluene layer was washed with water and concentrated. The residue was distilled (b.p. 110°–119° C./2.5 mmHg) to obtain 4.8 g of distillate. The IR spectrum of the product was identical with that of chrysanthemic acid. The composition of the optical isomers in the product was determined by the same method as described in EXAMPLE 1. (Composition: (+)-cis, 2.2%; (−)-cis, 2.2%; (+)-trans, 47.3%; (−)-trans, 48.3%).

EXAMPLE 6

In a 50 ml flask, there were charged chrysanthemic acid (composition: (+)-cis, 3.0%; (−)-cis, 22.0%; (+)-trans, 11.8%; (−)-trans, 63.2%) (5.0 g), dioxane (17.0 g) and t-butyl hydroperoxide (0.03 g) under nitrogen. A solution of boron tribromide (0.2 g) in dioxane (3.0 g) was added thereto at 15°–20° C. with stirring. After 30 minutes, the composition of the optical isomers of chrysanthemic acid in the reaction solution was determined by the same method as described in EXAMPLE 1. The composition was as follows: (+)-cis, 2.5%; (−)-cis, 2.6%; (+)-trans, 47.0%; (−)-trans, 47.9%. After 1 hour, the content of chrysanthemic acid in the reaction solution was determined by gas chromatography to be 4.6 g.

EXAMPLE 7

In a 50 ml flask, there were charged chrysanthemic acid (composition: (+)-cis, 3.0%; (−)-cis, 22.0%; (+)-trans, 11.8%; (−)-trans, 63.2%) (5.0 g), toluene (10.0 g) and cumene hydroperoxide (0.046 g) under nitrogen. A solution of boron tribromide (0.09 g) in toluene (1.7 g) was added thereto at 15°–20° C. with stirring. After 30 minutes, the composition of the optical isomers of chrysanthemic acid in the reaction solution was determined by the same method as described in EXAMPLE 1. The composition was as follows: (+)-cis, 3.0%; (−)-cis, 2.9%; (+)-trans, 45.8%; (−)-trans, 48.4%. After 1 hour, the content of chrysanthemic acid in the reaction solution was determined by gas chromatography to be 4.9 g.

EXAMPLE 8

In a 30 ml flask, there were charged ethyl chrysanthemate (composition: (+)-cis, 2.4%; (−)-cis, 7.6%; (+)-trans, 9.6%; (−)-trans, 70.4%) (2.0 g), toluene (4.7 g) and t-butyl hydroperoxide (0.06 g) under nitrogen. Boron tribromide (0.15 g) was added thereto at 20° C. with stirring and stirred for 1 hour. The reaction mixture was washed with water and concentrated under reduced pressure to leave a residue (1.95 g). The residue was added to a 10% sodium hydroxide aqueous solution and refluxed for 3 hours. The aqueous layer was washed with toluene. The aqueous layer was acidified with dilute hydrochloric acid and extracted with toluene. The toluene layer was washed with water and dried over anhydrous sodium sulfate. The solvent was evaporated under reduced pressure to leave a residue (1.6 g). The residue was distilled (b.p. 110°–119° C./2.5 mmHg) to obtain 1.54 g of distillate. The IR spectrum of the product was identical with that of chrysanthemic acid. The composition of the optical isomers in the product was determined by the same method as described in EXAMPLE 1. The result was as follows: (+)-cis, 3.4%; (−)-cis, 4.0%; (+)-trans, 45.4%; (−)-trans, 47.2%.

EXAMPLE 9

In a 30 ml flask, there were charged n-butyl chrysanthemate (composition: (+)-cis, 2.4%; (−)-cis, 17.6%; (+)-trans, 9.6%; (−)-trans, 70.4%) (2.0 g), dioxane (4.7 g) and t-butyl hydroperoxide (0.04 g) under nitrogen. Boron tribromide (0.10 g) was added thereto at 20° C. with stirring and stirred for 1 hour. The reaction mixture was washed with water and concentrated under reduced pressure to leave a residue (1.9 g). The residue was distilled (105°–106° C./2 mmHg) to obtain a distillate (1.79 g). The IR spectrum of the product was identical with that of n-butyl chrysanthemate. A small amount of the product was hydrolyzed by usual method to obtain chrysanthemic acid. The composition of the optical isomers in the product was determined by gas chromatography. The result was as follows: (+)-cis, 2.6%; (−)-cis, 3.4%; (+)-trans, 46.1%; (−)-trans, 47.9%.

EXAMPLE 10

In a 30 ml flask, there were charged ethyl chrysanthemate (composition: (+)-cis, 2.4%; (−)-cis, 17.6%; (+)-trans, 9.6%; (−)-trans, 70.4%) (2.0 g), n-heptane (18.0 g) and cumene hydroperoxide (0.08 g) under nitrogen. Boron tribromide (0.13 g) was added thereto at 40° C. with stirring and stirred for 1 hour. The reaction mixture was cooled to room temperature and washed with water and then was concentrated under reduced pressure to leave a residue (1.95 g). The residue was distilled (85°–88° C./10 mmHg) to obtain a distillate (1.80 g). The IR spectrum of the product was identical with that of ethyl chrysanthemate. The composition of the optical isomers in the product was determined by the same method as described in EXAMPLE 9. The result was as follows: (+)-cis, 3.0%; (−)-cis, 2.9%; (+)-trans, 46.1%; (−)-trans, 48.0%.

EXAMPLE 11

In a 50 ml flask, there were charged racemic chrysanthemic acid (composition: cis, 70.0%; trans, 30.0%) (2.0 g) and toluene (17.0 g) under nitrogen. A solution of boron tribromide (0.024 g) in toluene (1.0 g) was added thereto at 20° C. with stirring. After 2.5 hours, the reaction mixture was washed with diluted hydrochloric acid. 10% Sodium hydroxide aqueous solution (7.1 g) was added to the mixture at 40° C. with stirring. Then the aqueous layer was separated and acidified with diluted sulfuric acid and extracted with toluene. The toluene layer was washed with water and concentrated under reduced pressure. The residue was distilled (b.p. 110°–119° C./2.5 mmHg) to obtain 1.8 g of distillate. The IR spectrum of the product was identical with that of chrysanthemic acid. The composition of the geometrical isomers in the product was determined by gas chromatography. (cis, 7.0%; trans, 93.0%)

EXAMPLE 12

In a 50 ml flask, there were charged ethyl chrysanthemate (composition: cis, 40.7%; trans, 59.3%) (2.0 g) and toluene (17.0 g) under nitrogen. Boron tribromide (0.041 g) and toluene (1.0 g) were added thereto at 20° C. with stirring and stirred for 2 hours. The reaction mixture was washed with diluted hydrochloric acid and water successively. The solvent was evaporated under reduced pressure to leave a residue (2.03 g). The residue was distilled (85°-88° C./10 mmHg) to obtain a distillate (1.88 g).

The IR spectrum of the product was identical with that of ethyl chrysanthemate. The composition of the geometrical isomers in the product was determined by gas chromatography. The result was as follows: cis, 7.0%; trans, 93.0%.

EXAMPLE 13

In a 50 ml flask, there were charged chrysanthemic acid (composition: cis, 70.0%; trans, 30.0%) (2.0 g), toluene (17.0 g) and t-butyl hydroperoxide (0.005 g) under nitrogen. A solution of boron tribromide ((0.012 g) in toluene (1.0 g) was added thereto at 20° C. with stirring. After 1 hour, the reaction mixture was washed with diluted hydrochloric acid. 10% Sodium hydroxide aqueous solution (7.1 g) was added to the mixture at 40° C. with stirring and the aqueous layer was separated. The aqueoud layer was acidified with diluted sulfuric acid and extracted with toluene. The toluene layer was washed with water and concentrated under reduced pressure. The residue was distilled (b.p. 110°-119° C./2.5 mmHg) to obtain 1.82 g of distillate.

The IR spectrum of the product was identical with that of chrysanthemic acid. The composition of the geometrical isomers in the product was determined by gas chromatography. (cis, 6.0%; trans, 94.0%)

EXAMPLE 14

In a pb 50 ml flask, there were charged ethyl chrysanthemate (composition: cis, 40.7%; trans, 59.3%) (2.0 g), toluene (17.0 g) and t-butyl hydroperoxide (0.008 g) under nitrogen. Boron tribromide (0.023 g) and toluene (1.0 g) were added thereto at 20° C. with stirring and stirred for 1 hour. The reaction mixture was washed with diluted hydrochloric acid and water successively. The solvent was evaporated under reduced pressure to leave a residue (2.01 g). The residue was distilled (85°-88° C./10 mmHg) to obtain a distillate (1.93 g).

The IR spectrum of the product was identical with that of ethyl chrysanthemate. The composition of the geometrical isomers in the product was determined by gas chromatography. The result was as follows: cis, 6.5%; trans, 93.5%.

We claim:

1. A method for racemization of an optically active chrysanthemic acid or its ester of the formula:

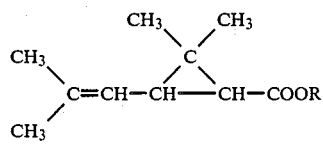

wherein R is a hydrogen atom; an alkyl group which may be substituted with a cycloalkyl group or with an aryl group, said alkyl group having from 1 to 20 total carbon atoms including the substituent; or a cycloalkyl group which may be substituted with an alkyl or with an alkoxy group, said cycloalkyl group having from 5 to 20 total carbon atoms including the substituent, which comprises contacting the acid or its ester described above with a boron bromide compound.

2. The method according to claim 1, wherein the contact is effected in the presence of an organic hydroperoxide.

3. The method according to claim 1, wherein the boron bromide compound is boron tribromide.

4. The method according to claim 2, wherein the substituent R in the formula (I) is hydrogen atom.

5. A method for the conversion of racemic cis isomer or of a mixture of the racemic cis and trans isomers of chrysanthemic acid or its ester of formula:

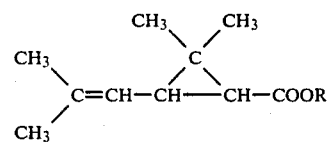

wherein R is a hydrogen atom; an alkyl group which may be substituted with a cycloalkyl group or with an aryl group, said alkyl group having from 1 to 20 total carbon atoms including the substituent; or a cycloalkyl group which may be substituted with an alkyl or with an alkoxy group, said cycloalkyl group having from 5 to 20 total carbon atoms including the substituent, into the corresponding racemic trans-rich isomer, which comprises contacting the acid or its ester described above with a boron bromide compound.

6. The method according to claim 5, wherein the boron bromide compound is boron tribromide.

7. The method according to claim 5, wherein the contact is effected in the presence of an organic hydroperoxide.

8. The method according to claim 2, wherein the boron bromide compound is boron tribromide.

9. The method according to claim 3, wherein the substituent R in the formula (I) is hydrogen atom.

10. The method according to claim 6, wherein the contact is effected in the presence of an organic hydroperoxide.

11. A method for racemization of an optically acitive chrysanthemic acid or its ester of the formula:

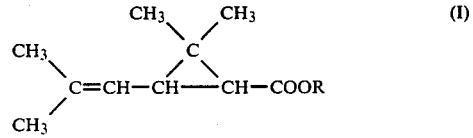

wherein R is a hydrogen atom; an alkyl group which may be substituted with a cycloalkyl group or with an aryl group, said alkyl group having from 1 to 20 total carbon atoms including the substituent; or a cycloalkyl group which may be substituted with an alkyl or with an alkoxy group, said cycloalkyl group having from 5 to 20 total carbon atoms including the substituent, which comprises contacting the acid or its ester described above with a boron bromide compound in the presence of an organic hydroperoxide.

12. The method according to claim 11, wherein said boron bromide compound is boron tribromide.

13. The method according to claim 11, wherein said organic hydroperoxide is a member selected from the group consisting of cumene hydroperoxide, diisopropylbenzene hydroperoxide, tert-butyl hydroperoxide, 1,1,3,3-tetramethyl butyl hydroperoxide, p-methane hydroperoxide, a hydroperoxide produced by oxidation of tetrahydrofuran, and a hydroperoxide produced by oxidation of dioxane.

14. The method according to claim 11, wherein said boron bromide compound is used in an amount of from 1/2000 to ¼ mol and said organic hydroperoxide is used in an amount of from 1/10 to 5 mol both amounts based upon a mol of the starting material to be treated.

15. A method for the conversion of racemic cis isomer or of a mixture of the racemic cis and trans isomers of chrysanthemic acid or its ester of formula:

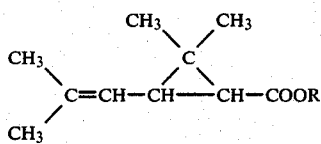

wherein R is a hydrogen atom; an alkyl group which may be substituted with a cycloalkyl group or with an aryl group, said alkyl group having from 1 to 20 total carbon atoms including the substituent; or a cycloalkyl group which may be substituted with an alkyl or with an alkoxy group, said cycloalkyl group having from 5 to 20 total carbon atoms including the substituent, into the corresponding racemic trans-rich isomer, which comprises contacting the acid or its ester described above with a boron bromide compound in the presence of an organic hydroperoxide.

16. The method according to claim 15, wherein said boron bromide compound is boron tribromide.

17. The method according to claim 15, wherein said organic hydroperoxide is a member selected from the group consisting of cumene hydroperoxide, diisopropylbenzene hydroperoxide, tert-butyl hydroperoxide, 1,1,3,3-tetramethyl butyl hydroperoxide, p-methane hydroperoxide, a hydroperoxide produced by oxidation of tetrahydrofuran, and a hydroperoxide produced by oxidation of dioxane.

18. The method according to claim 15, wherein said boron bormide compound is used in an amount of from 1/2000 to ¼ mol and said organic hydroperoxide is used in an amount of from 1/10 to 5 mol both amounts based upon a mol of the starting material to be treated.

19. The method according to claim 1, wherein the reaction temperature is from −30° C. to 100° C.

* * * * *